(12) United States Patent
Fukuyama

(10) Patent No.: US 7,276,380 B2
(45) Date of Patent: Oct. 2, 2007

(54) TRANSPARENT LIQUID INSPECTION APPARATUS, TRANSPARENT LIQUID INSPECTION METHOD, AND TRANSPARENT LIQUID APPLICATION METHOD

(75) Inventor: Teruaki Fukuyama, Awa-gun (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 596 days.

(21) Appl. No.: 10/110,326

(22) PCT Filed: Jul. 30, 2001

(86) PCT No.: PCT/JP01/06568

§ 371 (c)(1),
(2), (4) Date: Apr. 11, 2002

(87) PCT Pub. No.: WO02/14783

PCT Pub. Date: Feb. 21, 2002

(65) Prior Publication Data

US 2002/0151042 A1      Oct. 17, 2002

(30) Foreign Application Priority Data

Aug. 11, 2000    (JP)    ............................ 2000-243501

(51) Int. Cl.
*G01N 21/01* (2006.01)
*G01B 11/25* (2006.01)
*G01B 11/28* (2006.01)

(52) U.S. Cl. .................. 436/164; 356/601; 356/603; 356/612; 356/628; 356/635; 422/62; 422/82.05; 422/82.09; 436/1; 436/169

(58) Field of Classification Search .................. 422/62, 422/82.05, 82.09; 436/54, 164, 169, 1; 356/601, 356/610, 612, 614–615, 628, 635, 603
See application file for complete search history.

(56) References Cited

U.S. PATENT DOCUMENTS 4,361,110 A * 11/1982 Holmes ....................... 118/665
4,410,895 A * 10/1983 Houston et al. .............. 347/81

(Continued)

FOREIGN PATENT DOCUMENTS

JP        63-15380        1/1988

(Continued)

*Primary Examiner*—Arlen Soderquist
(74) *Attorney, Agent, or Firm*—Steptoe & Johnson LLP

(57) ABSTRACT

The present invention provides a transparent liquid inspection apparatus capable of identifying a boundary between a transparent liquid applied on a base material which provides a multi-piece product and the base material, and automatically inspecting an applied condition of the transparent liquid without influence of a background of the base material. A projected image of an illumination source (2) is reflected on a surface of the transparent liquid as a mirror, the projected image is picked up by cameras (41 to 44), and the image is analyzed by an image processing unit (8), thereby inspecting an amount of displacement of the transparent liquid from a predetermined application position and expansion of the surface of the transparent liquid.

7 Claims, 6 Drawing Sheets

U.S. PATENT DOCUMENTS

| | | | |
|---|---|---|---|
| 4,571,498 A * | 2/1986 | Hagan et al. | 250/559.21 |
| 4,824,230 A * | 4/1989 | Litt | 359/896 |
| 4,868,901 A * | 9/1989 | Kniskern et al. | 250/222.2 |
| 5,756,885 A * | 5/1998 | Poku et al. | 73/104 |
| 5,838,445 A * | 11/1998 | Sandhu et al. | 356/600 |
| 6,055,060 A * | 4/2000 | Bolduan et al. | 356/433 |
| 6,347,857 B1 * | 2/2002 | Purcell et al. | 347/19 |
| 6,521,187 B1 * | 2/2003 | Papen | 422/100 |
| 6,594,432 B2 * | 7/2003 | Chen et al. | 385/133 |
| 2002/0001544 A1 * | 1/2002 | Hess et al. | 422/100 |
| 2002/0089561 A1 * | 7/2002 | Weitzel et al. | 347/19 |
| 2003/0054567 A1 * | 3/2003 | Miyoshi et al. | 436/514 |

FOREIGN PATENT DOCUMENTS

| | | |
|---|---|---|
| JP | 3-120407 | 5/1991 |
| JP | 5-6913 | 1/1993 |
| JP | 6-341817 | 12/1994 |
| JP | 10-263954 | 10/1998 |
| JP | 11-330114 | 11/1999 |

* cited by examiner

TRANSPARENT LIQUID INSPECTION APPARATUS, TRANSPARENT LIQUID INSPECTION METHOD, AND TRANSPARENT LIQUID APPLICATION METHOD

TECHNICAL FIELD

The present invention relates to inspection of an applied condition after an application of a transparent liquid.

BACKGROUND ART

The present invention relates to an apparatus and a method of inspecting, after a transparent reagent for reaction with blood is applied on an electrode, an applied condition of the reagent (an amount of displacement of the transparent liquid from a predetermined application position and surface expansion of the transparent liquid), for example in a manufacturing process of a blood glucose value sensor for measuring a blood glucose value of a human.

As shown in FIG. 6, in a process of manufacturing, from one base material 7, a large number of pieces of a multi-piece product 22 each applied with a transparent liquid 50, applied conditions of the transparent liquid have been visually inspected by an inspector.

However, inspection accuracy and inspection efficiency are low in the visual inspection by the inspector, and thus reliable products cannot be produced, and also production speed is low to prevent high volume production. In this view, inspection of an applied condition with high accuracy using an automated instrument is desired for ensuring reliability of a product and increasing production efficiency. Thus, attempts have been made to automate inspection of an applied condition using an image processing technique.

To automatically inspect the applied condition by the image processing technique, a boundary between the base material and the transparent liquid needs to be identified. For this purpose, a method has been considered in which surface tension of the transparent liquid is used and an end of the transparent liquid is illuminated to cause the boundary to emerge for identification.

However, when the surface tension of the transparent liquid is low, the transparent liquid penetrates the base material, and the boundary between the base material and the transparent liquid does not emerge even if the end of the transparent liquid is illuminated, thereby causing difficulty in identifying the boundary between the base material and the transparent liquid. Further, the base material actually has a background (for example, a printed electrode pattern in the blood glucose value sensor), and thus a contrast between the base material and the transparent liquid and also a contrast to the background need to be considered, thereby further causing difficulty in identifying the boundary by the image processing technique. Therefore, a method of automatically inspecting the applied condition of the transparent liquid by the image processing technique has not yet been established.

DISCLOSURE OF INVENTION

The present invention solves the above described problems, and has an object to provide a transparent liquid inspection apparatus capable of, even if surface tension of a transparent liquid applied on a base material to provide a multi-piece product is low, identifying a boundary between the base material and the transparent liquid and automatically inspecting an applied condition of the transparent liquid without influence of a background of the base material by projecting a shape of illuminating means on a surface of the transparent liquid as a mirror, picking up a projected image, and processing and analyzing a pickup image.

A transparent liquid inspection apparatus according to one embodiment is characterized by comprising: a base material providing a multi-piece product, each piece being applied with a transparent liquid; illuminating means for illuminating the transparent liquid; image pickup means for picking up an image of a shape of the illuminating means projected on a surface of the transparent liquid; and calculating means for calculating a luminance component of a boundary between the base material and the transparent liquid based on the image from the image pickup means, calculating surface expansion of the transparent liquid based on the luminance component, and statistically processing data on the surface expansion of the transparent liquid to calculate an amount of displacement of the whole of the transparent liquid from a predetermined application position.

A transparent liquid inspection apparatus according to another embodiment is characterized in that in the described transparent liquid inspection apparatus, the base material is divided into a plurality of blocks in accordance with image pickup fields of the image pickup means, and a desired number of image pickup means and illuminating means corresponding to the blocks are provided, thereby allowing images of the desired number of blocks to be simultaneously picked up.

A transparent liquid inspection method according to one embodiment is characterized by comprising the steps of: illuminating a transparent liquid applied on each piece of a multi-piece product provided by a base material; picking up an image of a shape of illuminating means projected on a surface of the transparent liquid; calculating a luminance component of a boundary between the base material and the transparent liquid based on the image picked up; calculating surface expansion of the transparent liquid based on the luminance component; and statistically processing data on the surface expansion of the transparent liquid to calculate an amount of displacement of the whole of the transparent liquid from a predetermined application position.

A transparent liquid inspection method according to another embodiment is characterized in that in the described method, an amount of displacement of the whole of the transparent liquid from a predetermined application position is fed back to a step of applying a transparent liquid on each piece of the multi-piece product provided by the base material.

According to the invention, even if the surface tension of the transparent liquid applied on the base material providing a multi-piece product is low, the boundary between the base material and the transparent liquid can be identified, and the applied condition of the transparent liquid can be automatically inspected at high speed with high accuracy and high stability without influence of the background of the base material.

BEST MODE FOR CARRYING OUT THE INVENTION

Now, an embodiment of the present invention will be described in detail with reference to the drawings.

Figure 1:
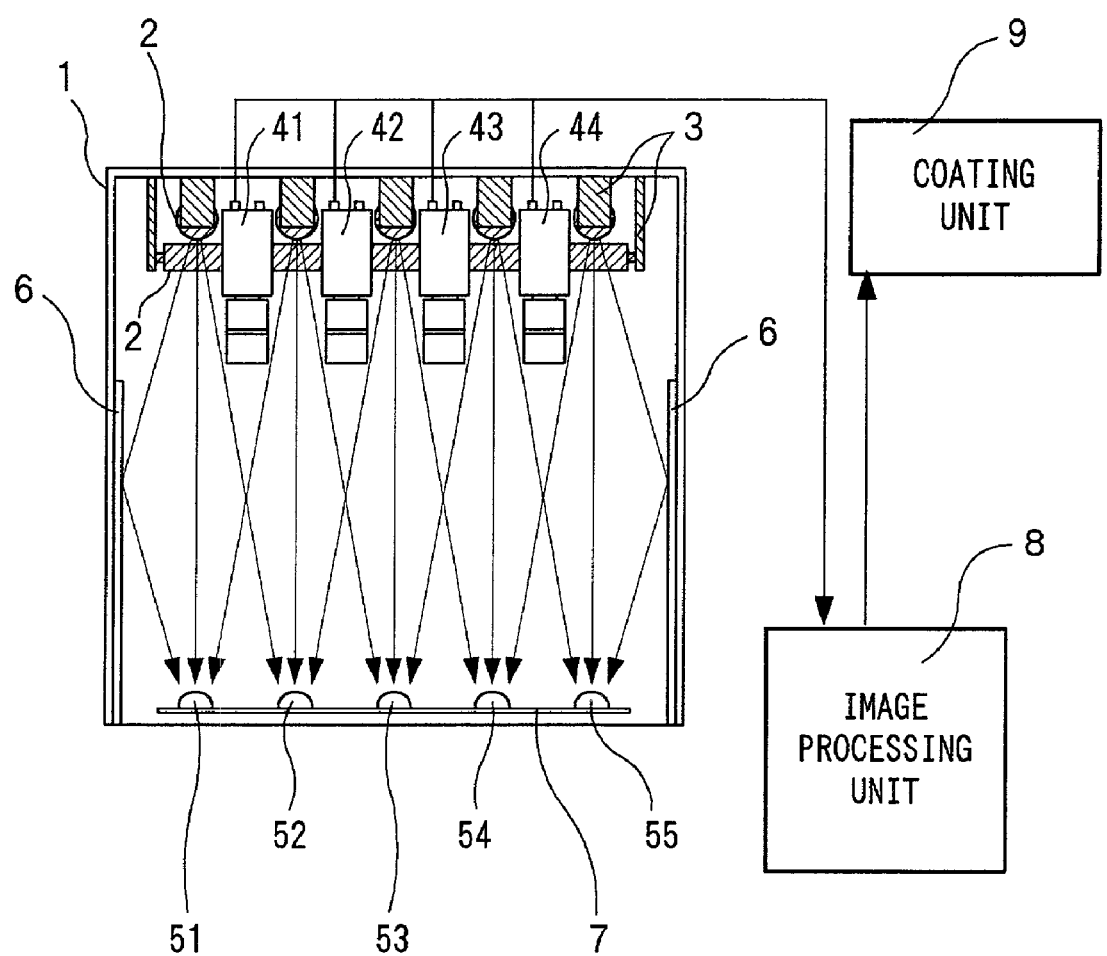
FIG. 1 is a sectional view of a transparent liquid inspection apparatus according to an embodiment of the invention.

FIG. 1 is a sectional view of a transparent liquid inspection apparatus according to an embodiment of the present invention. Reference numeral 1 denotes an illuminating unit; 2, an illumination source (illuminating means); 3, a support for supporting the illumination source 2; 41 to 44, cameras having a function of an electronic shutter (image pickup means); 51 to 55, transparent liquids applied; 6, an illumination reflector; 7, a base material conveyed in the illuminating unit 1 by a conveyer (not shown) that is a conveying unit placed below the illuminating unit 1; 8, an image processing unit (calculating means) for analyzing applied conditions of the transparent liquids from images obtained by the cameras 41 to 44; and 9, an application unit for applying the transparent liquid on a predetermined position on the base material 7.

In this embodiment, in manufacturing a multi-piece product applied with the transparent liquid, the transparent liquid inspection apparatus shown in FIG. 1 is used, the base material 7 applied with a predetermined amount of transparent liquid on the predetermined position by the application unit 9 is conveyed by the conveying unit, the transparent liquid is illuminated by the illumination source 2 when the transparent liquid passes through a predetermined measuring position, a shape of the illumination source 2 is projected on a surface of the transparent liquid as a mirror, a projected image on the surface is picked up by the camera, and the image is analyzed by the image processing unit 8, thereby automatically inspecting the applied condition of the transparent liquid.

The illuminating unit 1 includes the illumination source 2, support 3, and illumination reflector 6. The illuminating unit 1 needs non-flickering light with high luminance as the illumination source, so that a plurality of fluorescent lights with an inverter are used. The fluorescent lights are placed in a crossing manner vertically above the transparent liquid to be inspected, and their lengths, widths, and heights can be fine adjusted by the support 3 in accordance with an application pattern (arrangement condition) of the transparent liquid. To increase inspection accuracy of the transparent liquid, output of the illumination source 2 may be adjusted to adjust a contrast of the projected image on the surface of the transparent liquid. For amounts of illumination on the transparent liquid applied near a center of the base material and on the transparent liquid applied on a periphery of the base material to be equal, the illumination reflector 6 formed by a mirror is provided on each inner side of the illuminating unit 1.

The cameras 41 to 44 for picking up images are located so as not to block the light from above. That is, the illumination sources 2 are located in predetermined spaces among the cameras 41 to 44. The cameras 41 to 44 are located in such a manner that a center of an image capturing divided block described below is on a central axis of an image pickup field of each camera.

Figure 2:
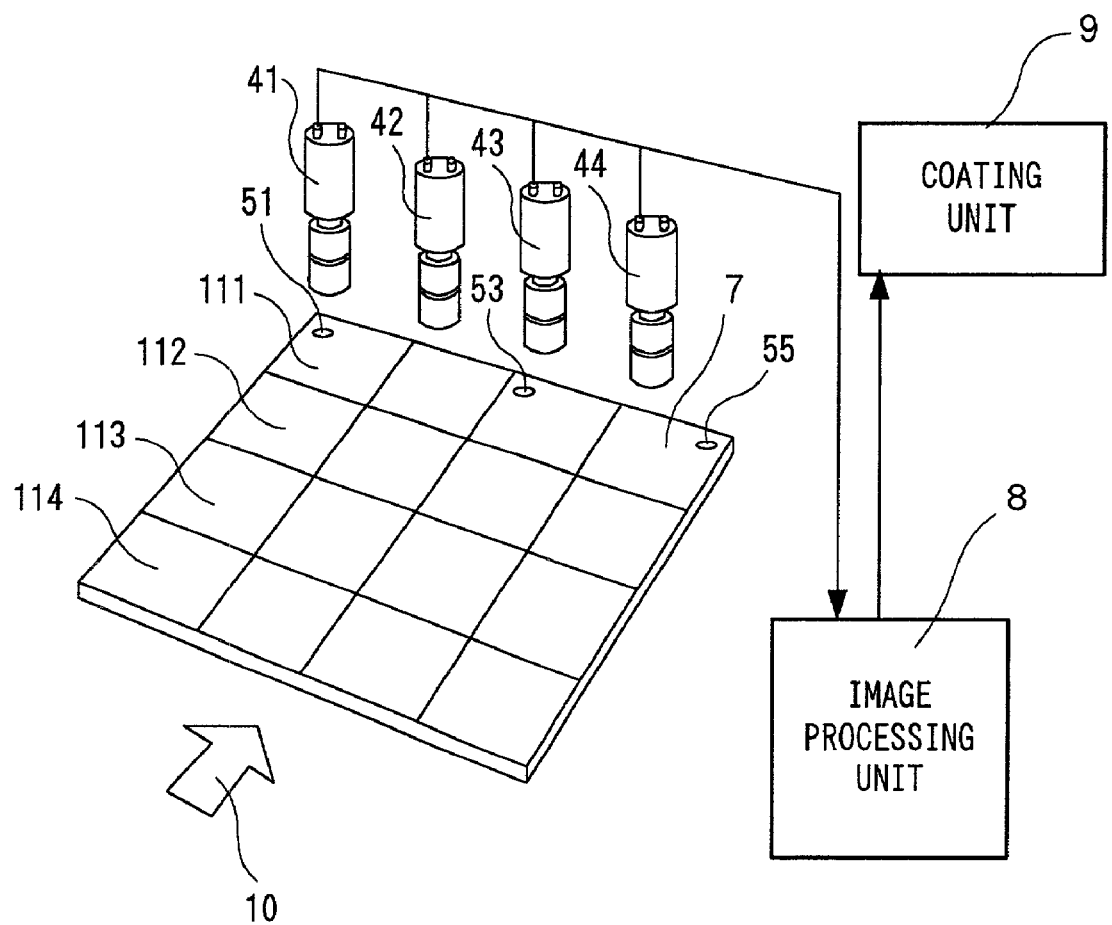
FIG. 2 illustrates an operation when a base material is captured in a divided manner by cameras in the embodiment of the invention.

FIG. 2 illustrates an operation when the base material 7 is captured in a divided manner by the cameras 41 to 44 in the embodiment of the invention. In FIG. 2, reference numerals 111, 112, 113, 114 denote image capturing divided blocks of the camera 41, and reference numeral 10 denotes a conveying direction of the base material 7.

The four cameras 41 to 44 are located vertically above the image capturing divided blocks aligned in a horizontal direction of the base material 7 (a direction orthogonal to the conveying direction 10) so as to correspond to respective divided areas when the base material 7 is divided into four parts in the horizontal direction (the direction orthogonal to the conveying direction 10).

Each of the cameras 41 to 44 thus located determines image capturing divided blocks that are measuring fields maintaining sufficient resolution for inspection with respect to the conveying direction 10 of the base material 7. However, sufficient inspection accuracy cannot be maintained unless a sufficient amount of light is supplied to each image capturing divided block. Thus, to supply a sufficient amount of light to the image capturing divided block, as described above, the plurality of fluorescent lights with an inverter are used as the illumination source 2 for each of the cameras 41 to 44 and located in the crossing manner in the predetermined spaces between the cameras 41 to 44, and placement of the illumination source 2 is fine adjusted in accordance with the application pattern of the transparent liquid.

When the base material 7 is divided by the image capturing divided blocks as described above and conveyed in the direction 10, an image capturing divided block corresponding to each of the cameras 41 to 44 is placed vertically below each of the cameras 41 to 44 (within the image pickup field), then each of the cameras 41 to 44 simultaneously releases the electronic shutter and picks up the image of the transparent liquid that is applied on each image capturing divided block and on which the shape of the illumination source 2 is projected. Each picked up image captured is transferred to the image processing unit 8, and temporarily stored in a memory (not shown) in the image processing unit 8. The image processing unit 8 inspects the applied condition of the transparent liquid on each image capturing divided block in accordance with an image processing program based on each picked up image (the shape of the illumination source 2 projected on the surface of the transparent liquid).

For example, the camera 41 determines the image capturing divided blocks 111, 112, 113, 114 in the conveying direction 10 of the base material 7, and releases the electronic shutter with the timing of conveyance of the image capturing divided blocks to capture the images. Specifically, when the image capturing divided block 111 reaches within the image pickup field of the camera 41, the electronic shutter is released at that moment, the image of the transparent liquid on the image capturing divided block 111 (the shape of the illumination source 2 projected on the surface of the transparent liquid) is captured, and the captured image is analyzed by the image processing unit 8, thereby inspecting the applied condition of each transparent liquid on the image capturing divided block 111. Next, when the base material 7 is conveyed by a conveyer for conveyance (not shown), and the image capturing divided block 112 reaches within the image pickup field of the camera 41, the same processing operation as for the image capturing divided block 111 is performed. This processing operation is repeated up to an end of the base material 7. This processing method allows inspection of the applied condition of the transparent liquid without stopping a flow of steps, and prevents influence on a process of drying the transparent liquid.

As described above, in this embodiment, the images of the large numbers of transparent liquids on which surfaces the shape of the illumination source 2 is projected can be picked up with satisfactory inspection accuracy, and the applied conditions of the large numbers of transparent liquids can be inspected in a short time.

In this embodiment, the four cameras are arranged in a line in a horizontal direction with respect to the base material, but not limited to a single line, the number of lines may be increased. The number of cameras are not limited to four.

Figure 3:
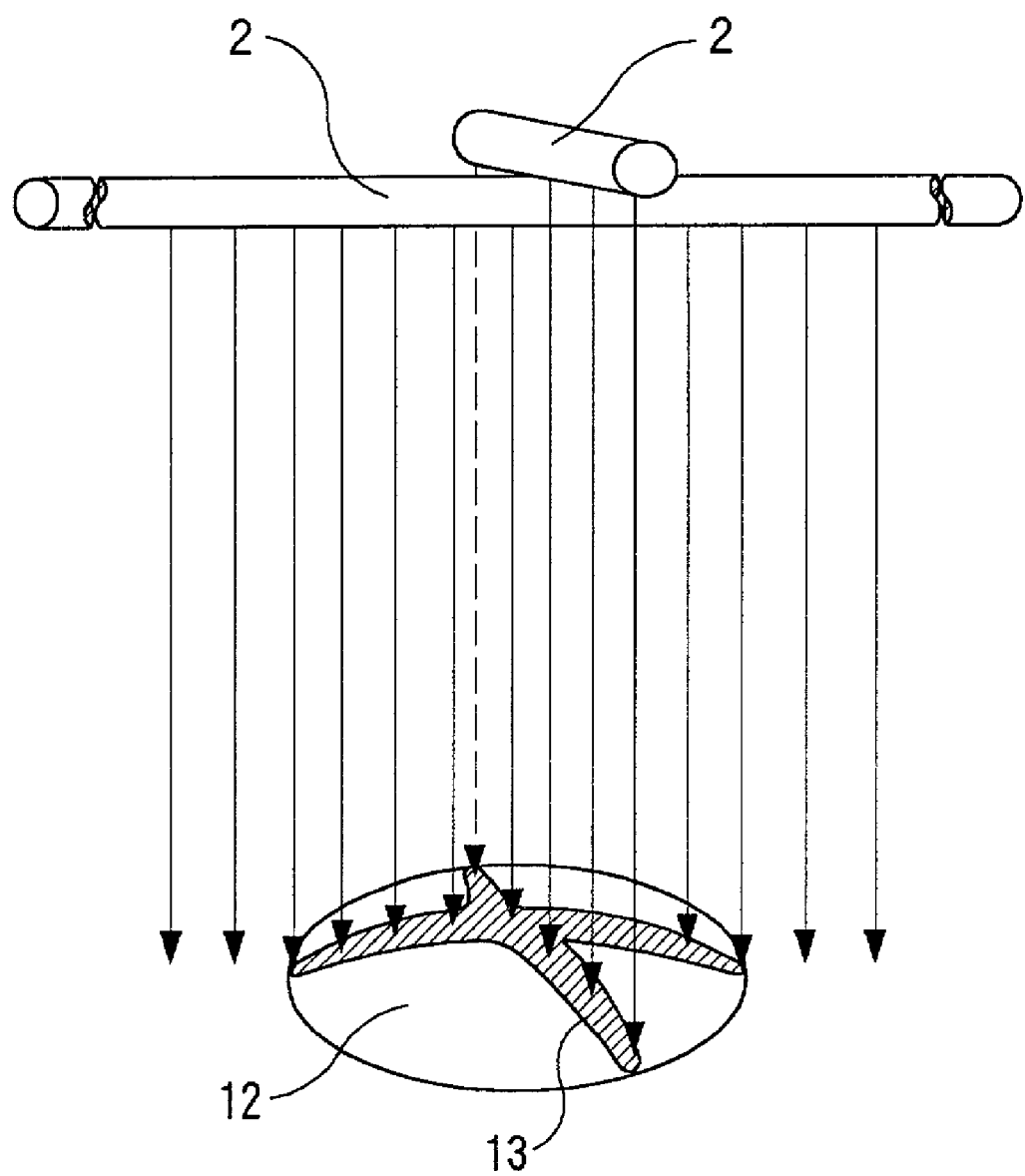
FIG. 3 schematically shows a surface condition of an arbitrary transparent liquid according to the embodiment of the invention.

FIG. 3 schematically shows a surface condition of the transparent liquid that is applied on the base material 7 to provide the multi-piece product and on which surface a shape of a chosen illumination source is projected according to the embodiment of the invention, and reference numeral 2 denotes an illumination source; 12, a chosen transparent liquid; and 13, a projected image by the illumination source 2 on the surface of the chosen transparent liquid 12. In this embodiment, as shown in FIG. 3, the shape of the illumination source 2 is projected on the surface of each transparent liquid.

When the transparent liquid is illuminated vertically from above, if a material of the base material 7 is an opalescent PET sheet, intensity of a reflection light from the base material (PET sheet) 7 is higher than that of a reflection light from the surface of the transparent liquid. For difference in luminance of the picked up images captured by the cameras 41 to 44, the surface is dark and the PET sheet is more bright, thereby allowing identification of the end of the surface and inspection of the applied condition of the transparent liquid.

However, when a solvent such as carbon is applied on a substrate to be applied with the transparent liquid, the carbon is darker than the surface of the transparent liquid, and the intensity of the reflection light from the surface of the transparent liquid as well as intensity of the reflection light from the base material are low to prevent the inspection. In this embodiment, the fluorescent lights with the inverter are used as the illumination source, and the transparent liquid is illuminated from above to project the shape of the illumination source by the fluorescent lights with the inverter on the surface of the transparent liquid (see FIG. 3). Then, the images of the large numbers of transparent liquids on which the shape of the illumination source is projected are picked up by the cameras and transferred to the image processing unit. The image processing unit detects surface expansion of each transparent liquid from the projected image of the illumination source on the surface of the transparent liquid, statistically processes the surface expansion of the transparent liquid, and inspects an amount of displacement of the whole of the transparent liquid whose image is picked up from a predetermined application position (displacement of an actually applied position from a predetermined position to be applied with the transparent liquid).

Figure 4:
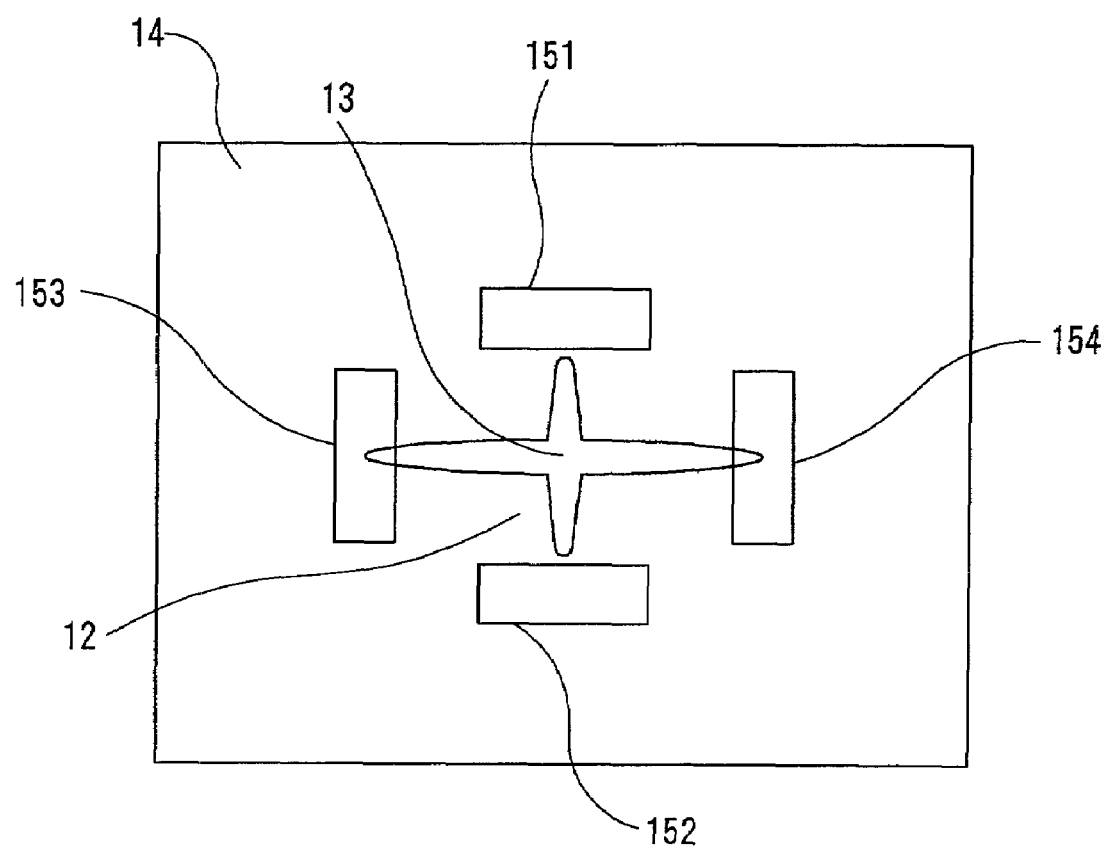
FIG. 4 schematically shows a surface condition of a chosen transparent liquid displayed on a screen of a image processing unit according to the embodiment of the invention.

Now, a method of identifying the boundary between the base material and the transparent liquid and obtaining the surface expansion of the transparent liquid in the image processing unit will be described with reference to FIG. 4 and FIG. 5. FIG. 4 shows a state where any one of the transparent liquids reflected on pickup images transferred from the cameras is displayed on the screen of the image processing unit. In FIG. 4, reference numeral 12 denotes an arbitrary transparent liquid; 13, a projected image by the illumination source on the surface of the chosen transparent liquid 12; 14, a screen of the image processing unit; and 151, 152, 153, 154, application detecting cursors set around ends of a predetermined position to be applied with the chosen transparent liquid 12 on the screen 14 of the image processing unit.

For the expansion of the liquid, detection of its length and width is sufficient, so that in this embodiment, the illumination source 2 is formed in the crossing manner, the application detecting cursors are placed on four positions at 90° intervals, and the boundary between the base material 7 and the chosen transparent liquid 12 is identified at the four positions. The positions to be identified are not limited to the four positions as proposed, but any position may be possible as long as expansion along the length and width can be detected. That is, the shape of the illumination source may match the expansion along the length and width of the transparent liquid, and identification positions may be set taking advantage of the shape. For example, a star illumination source is used to set identification positions at tips of the star (five positions).

To identify the boundary between the base material 7 and the arbitrary transparent liquid 12, it is determined whether the projected image 13 is displayed with overlapping each area of the application detecting cursors 151, 152, 153, 152 on the screen 14 of the image processing unit. Specifically, each area of the application detecting cursors 151, 152, 153, 154 is processed by histogram mentioned below to identify the boundary between the base material 7 and the arbitrary transparent liquid 12.

Figure 5A:
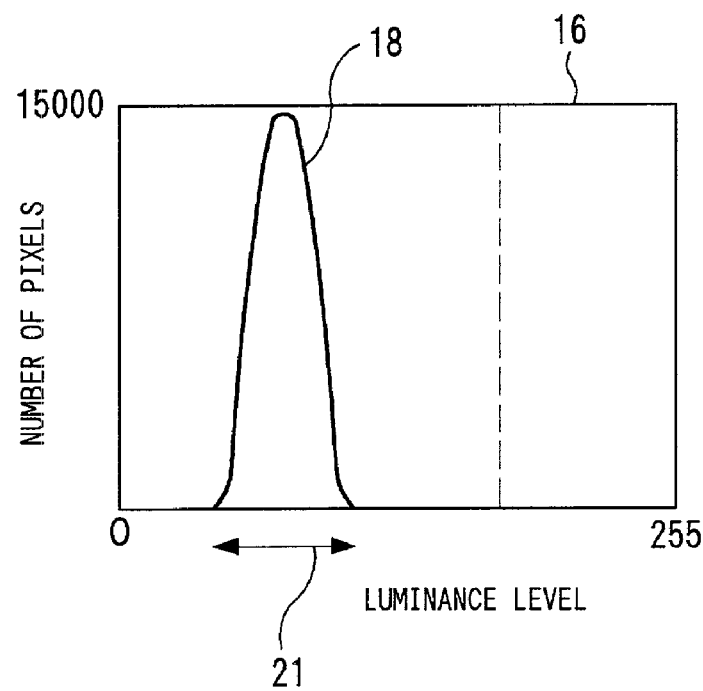
FIG. 5(a) and FIG. 5(b) show results of histogram processing of an end of a transparent liquid according to the embodiment of the invention.

For example, in FIG. 4, the projected image 13 is not displayed with overlapping each area of the application detecting cursors 151, 152 since the surface expansion of the arbitrary transparent liquid 12 is small, and histogram processing provides histogram data 16 as shown in FIG. 5(a). In this graph, the ordinate represents the number of pixels and the abscissa represents luminance levels. Results of the histogram processing in this case show one crest of data 18 by a luminance component of the base material 7, thereby reducing a contrast 21.

Figure 5B:
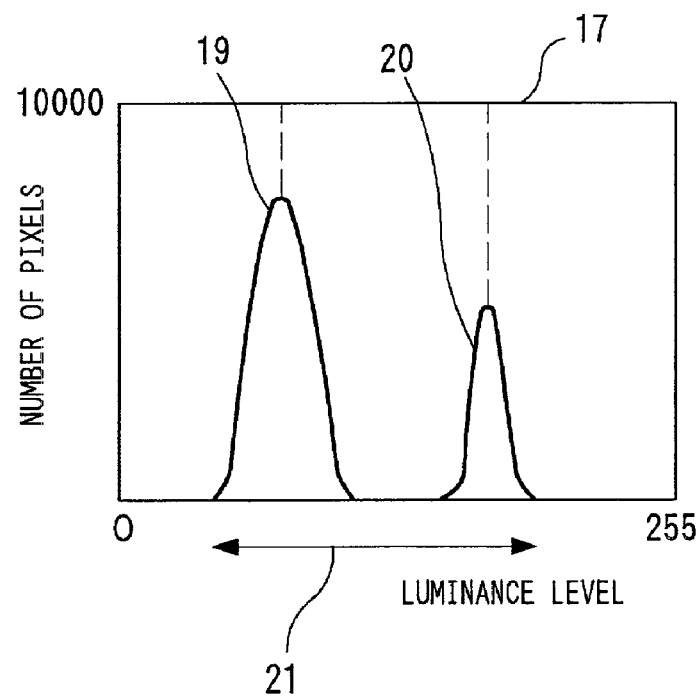
Figure 6:
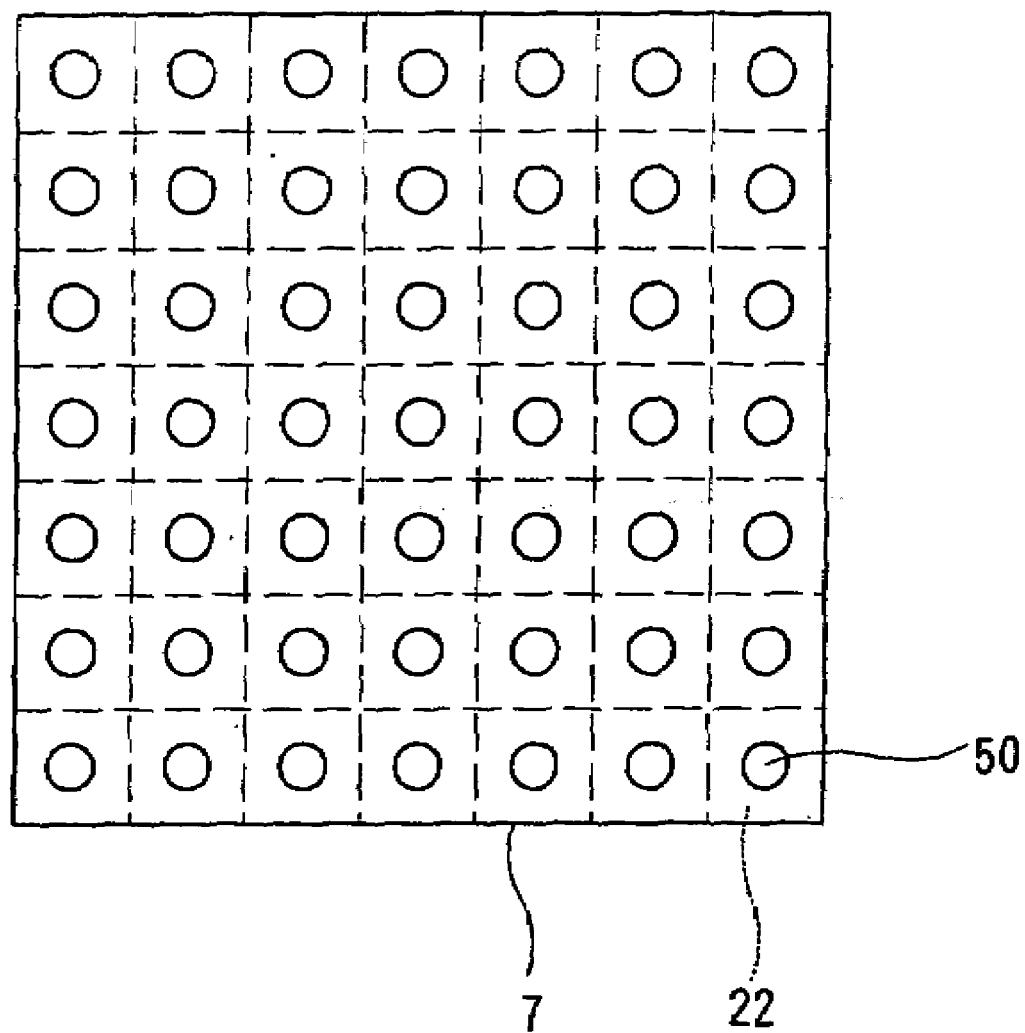
FIG. 6 schematically shows a base material applied with a transparent liquid.

In each area of the application detecting cursors 153, 154, the arbitrary transparent liquid 12 is normally applied, and the projected image 13 is displayed with overlapping each area. Histogram processing of each area of the application detecting cursors 153, 154 provides histogram data 17 as shown in FIG. 5(b). Results of the histogram processing in this case show two crests by a luminance component 19 of the base material 7 and a luminance component 20 of the projected image 13, thereby increasing a contrast 21 in each area of the application detecting cursors 153, 154. In this way, the histogram processing is performed to identify the boundary between the base material and the transparent liquid from the size of the data on the contrast 21 and to obtain the surface expansion of the transparent liquid.

From the data on the expansion of the transparent liquid at four corners of the base material 7, a barycentric position of the projected image on the surface of the transparent liquid is obtained, and barycentric data is statistically processed, and thus the amount of displacement of the whole of the transparent liquid from the predetermined application position (displacement of the actually applied position from the predetermined position to be applied with the transparent liquid by nature) is calculated and fed back to the application unit 9.

It is also possible to perform labeling processing of the projected image by the illumination source on the surface of the transparent liquid, and detect the expansion along the length and width to thereby obtain the surface expansion of the transparent liquid and the amount of displacement from the predetermined position. The labeling processing is a processing method of determining the projected images up to a gap as a group in detecting the projected images.

In the transparent liquid inspection apparatus configured as described above according to this embodiment, the image of the surface of the transparent liquid that is illuminated by the illumination source 2 and on which the shape of the illumination source 2 is projected is picked up by each of the cameras 41 to 44, and the picked up image is processed by the image processing unit 8, thereby automatically inspecting the applied condition of the transparent liquid.

Furthermore, in this embodiment, the amount of displacement of the transparent liquid from the predetermined application position is fed back to the application unit 9 to thereby control the application unit 9. This allows quick response to the displacement of the applied position of the transparent liquid from the predetermined position, and allows stable application of the transparent liquid (see FIG. 1).

As described above, according to the present invention, the illuminating unit is located above the transparent liquid applied on the base material which provides the multi-piece product, the transparent liquid is illuminated, the shape of the illuminating unit is projected on the surface of the transparent liquid, and the projected image is picked up to be processed, thereby allowing automatic inspection of the applied condition of the transparent liquid at a high speed with high accuracy and high stability. Therefore, for example, in a process of manufacturing a blood glucose value sensor, an applied condition of a transparent reagent containing CMC carboxymethylcellulose or the like or glucose oxidase formed on an electrode can be automatically inspected at high speed.

The invention claimed is:

1. A transparent liquid inspection apparatus, comprising:
a base material having a multiplicity of section pieces placed in predetermined locations, each section piece having applied thereto a transparent liquid capable of surface expansion;
illuminating means having a predetermined shape, for illuminating a surface of the base material so that the shape is projected on the surface of the transparent liquid in each section piece, the projected shape of said illuminating means having a plurality of tips;
image pickup means for picking up an image of the surface of the base material and transmitting the image of a predetermined number of section pieces of said base material applied with the transparent liquid;
means for calculating, based on the image transmitted from said image pickup means, a luminance component in a plurality of locations in each section piece, each location being defined by a cursor for performing histogram processing and comprising an area to be transmitted as an image, the location comprising a part of a boundary of the transparent liquid applied at a predetermined application position thereof in each section piece and including one of the tips of the projected shape of the illuminating means on the surface of the transparent liquid in each section piece, wherein the luminance component is calculated by measuring a first luminance of the illuminated base material located in the cursor and a second luminance of a tip of the projected share on the surface of the transparent liquid located in the cursor;
means for calculating, based on the calculated luminance component, the surface expansion of the transparent liquid in each section piece; and
means for statistically processing data on the surface expansion of the transparent liquid in the predetermined number of section pieces to calculate an amount of displacement of the transparent liquid from the predetermined application position thereof in each section piece.

2. The transparent liquid inspection apparatus according to claim 1, wherein said base material is divided into a plurality of blocks in accordance with image pickup fields of said image pickup means, and a desired number of said pickup means and said illuminating means each corresponding to said blocks are provided, thereby allowing images of said desired number of said blocks to be simultaneously picked up.

3. The transparent liquid inspection apparatus according to claim 1, wherein the illuminating means has a cross shape.

4. A transparent liquid inspection method, comprising the steps of:
providing a base material with a surface thereof facing upward, said base material having a multiplicity of section pieces in predetermined locations, each section piece having applied thereto a transparent liquid capable of surface expansion;
illuminating the surface of said base material by illuminating means having a predetermined shape so that the shape is projected on the surface of the transparent liquid in each section piece, the projected shape of said illuminating means having a plurality of tips;
picking up an image of the surface of said base material illuminated by said illuminating means and transmitting the image of a predetermined number of section pieces of said base material applied with the transparent liquid;
calculating, based on the transmitted image, a luminance component in a plurality of locations in each section piece, each location being defined by a cursor for performing histogram processing and comprising an area to be transmitted as an image, the location comprising a part of a boundary of the transparent liquid applied at a predetermined application position thereof in each section piece and including one of the tips of the projected shape of the illuminating means on the surface of the transparent liquid in each section piece, wherein the luminance component is calculated by measuring a first luminance of the illuminated base material located in the cursor and a second luminance of a tip of the projected shape on the surface of the transparent liquid located in the cursor;
calculating, based on the luminance component, the surface expansion of said transparent liquid in each section piece; and
statistically processing data on the surface expansion of said transparent liquid in the predetermined number of section pieces to calculate an amount of displacement of the transparent liquid from the predetermined application position thereof in each section piece.

5. The transparent liquid inspection method according to claim 4, wherein the illuminating means has a cross shape.

6. A transparent liquid inspection method, comprising the steps of:

applying a transparent liquid on each of a multiplicity of section pieces on predetermined locations on a base material, the transparent liquid capable of surface expansion;

illuminating an upward facing surface of said base material by illuminating means having a predetermined shape so that the shape is projected on the surface of the transparent liquid in each section piece, the projected shape of said illuminating means having a plurality of tips;

picking up an image of the surface of said base material illuminated by said illuminating means and transmitting the image of a predetermined number of section pieces of said base material applied with the transparent liquid;

calculating, based on the transmitted image, a luminance component in a plurality of locations in each section piece, each location being defined by a cursor for performing histogram processing and comprising an area to be transmitted as an image, the location comprising a part of a boundary of the transparent liquid applied at a predetermined application position thereof in each section piece and including one of the tips of the projected shape of the illuminating means on the surface of the transparent liquid in each section piece;

calculating, based on the luminance component, the surface expansion of said transparent liquid in each section piece;

statistically processing data on the surface expansion of said transparent liquid in the predetermined number of section pieces to calculate an amount of displacement of the transparent liquid from the predetermined application position thereof in each section piece; and feeding back the calculated amount of displacement of the transparent liquid from the predetermined application position thereof in each section piece, to the step of applying a transparent liquid on each of a multiplicity of the section pieces on predetermined locations on the base material.

7. The transparent liquid inspection method according to claim 6, wherein the illuminating means has a cross shape.

* * * * *